US008877511B2

(12) United States Patent
Bedre et al.

(10) Patent No.: US 8,877,511 B2
(45) Date of Patent: Nov. 4, 2014

(54) METHOD AND SYSTEM FOR MANUFACTURE AND USE OF MACROPOROUS BEADS IN A MULTIPLEX ASSAY

(75) Inventors: Jason Bedre, Georgetown, TX (US); Don Chandler, Austin, TX (US); Ben Mize, Austin, TX (US)

(73) Assignee: Luminex Corporation, Austin, TX (US)

( * ) Notice: Subject to any disclaimer, the term of this patent is extended or adjusted under 35 U.S.C. 154(b) by 184 days.

(21) Appl. No.: 12/615,844

(22) Filed: Nov. 10, 2009

(65) Prior Publication Data

US 2010/0120165 A1    May 13, 2010

Related U.S. Application Data

(60) Provisional application No. 61/113,027, filed on Nov. 10, 2008.

(51) Int. Cl.
*G01N 21/76* (2006.01)
*G01N 33/543* (2006.01)

(52) U.S. Cl.
CPC .............................. *G01N 33/54313* (2013.01)
USPC ........................................... 436/172; 521/56

(58) Field of Classification Search
None
See application file for complete search history.

(56) References Cited

U.S. PATENT DOCUMENTS

| | | |
|---|---|---|
| 4,459,378 A | 7/1984 | Ugelstad |
| 4,774,265 A | 9/1988 | Ugelstad et al. |
| 5,736,330 A | 4/1998 | Fulton |
| 5,981,180 A | 11/1999 | Chandler et al. |
| 6,057,107 A | 5/2000 | Fulton |
| 6,268,222 B1 | 7/2001 | Chandler et al. |
| 6,449,562 B1 | 9/2002 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler |
| 6,592,822 B1 | 7/2003 | Chandler |
| 6,632,526 B1 | 10/2003 | Chandler et al. |
| 6,649,414 B1 | 11/2003 | Chandler et al. |
| 6,773,812 B2 | 8/2004 | Chandler et al. |
| 6,939,720 B2 | 9/2005 | Chandler et al. |
| 7,141,431 B2 | 11/2006 | Chandler et al. |
| 7,241,883 B2 | 7/2007 | Lugade et al. |
| 7,274,316 B2 | 9/2007 | Moore |

(Continued)

FOREIGN PATENT DOCUMENTS

| | | |
|---|---|---|
| CA | 2672034 | 6/2008 |
| CN | 101241078 | 8/2008 |

(Continued)

OTHER PUBLICATIONS

Hosoya, K. et al. In situ surface-selective modification of uniform size macroporous polymer particles with temperature-responsive poly-N-isopropylacrylamide, 1994, macromolecules, vol. 27(14), pp. 3973-3976.*

(Continued)

*Primary Examiner* — Robert Xu
(74) *Attorney, Agent, or Firm* — Parker Highlander PLLC

(57) ABSTRACT

Macroporous beads and a method of manufacturing and using such macroporous beads. wherein the beads are distinguishable for use in a multiplex assay. Preferably, the beads are distinguishable by two or more unique fluorochromes, and at least some of the beads are magnetically responsive. In a preferred form, some of the macroporous beads have interior pores with a different moiety from the exterior surface, allowing beads with different attached functional groups.

8 Claims, 2 Drawing Sheets

2µm 6000\

(56) References Cited

U.S. PATENT DOCUMENTS

| | | | |
|---|---|---|---|
| 7,955,802 B2* | 6/2011 | Whitman et al. | 435/6.12 |
| 2004/0126904 A1 | 7/2004 | Watkins et al. | 436/526 |
| 2004/0142341 A1* | 7/2004 | Schmitt et al. | 435/6 |
| 2006/0269962 A1 | 11/2006 | Watkins et al. | 435/6 |
| 2006/0275820 A1 | 12/2006 | Watkins et al. | 435/5 |
| 2010/0129794 A1* | 5/2010 | Fabis et al. | 435/6 |

FOREIGN PATENT DOCUMENTS

| | | |
|---|---|---|
| EP | 1 139 100 | 10/2001 |
| EP | 1139100 | 10/2001 |
| WO | WO 02-088734 | 11/2002 |
| WO | WO 2007-038523 | 4/2007 |
| WO | WO 2007/065933 | 6/2007 |

OTHER PUBLICATIONS

Tuncel et al., "Carboxyl carrying-large uniform latex particles," Colloids and Surfaces A: Physicochemical and Engineering Aspects, vol. 197, 2002, pp. 79-94.

Cheng et al., "Synthesis and Characterization of Monodisperse Porous Polymer Particles," Journal of Polymer Science: Part A: Polymer Chemistry, vol. 30, 1992, pp. 235-244.

Kim et al., "Monodisperse micron-sized macroporous poly(styrene-co-divinylbenzene) particles by seeded polymerization," *Colloid Polym Sci.*, 279:146-152, 2001.

PCT International Preliminary Report on Patentability issued in International application No. PCT/US2009/063899, dated May 19, 2011.

Extended Search Report issued in European Patent Application No. 09825598.7, dated May 5, 2012.

Office Communication issued in Chinese Patent Appliciition No. 200980144541.9, dated May 13, 2013. (English translation).

Wang et al., "Mono-dispersed cross-linked polysterene microspheres prepared by seed swelling polymerization method,"*Journal of Dalian Polytechnic University*, 24(11):1289-1294, 2007. (English abstract of Chinese publication).

Office Communication issued in European Patent Application No. 09 825 598.7, dated Jun. 13, 2013.

\* cited by examiner

2μm 6000\

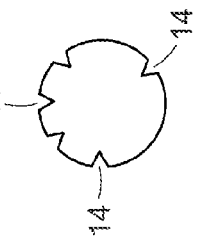
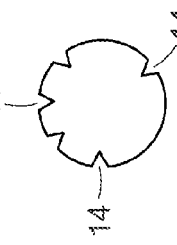
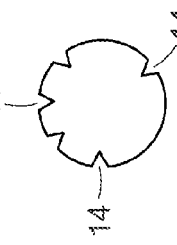
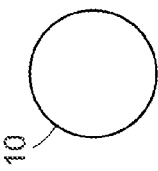
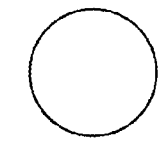
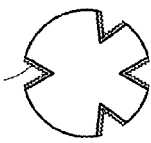
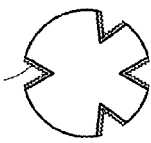
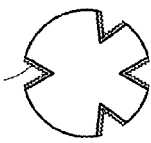
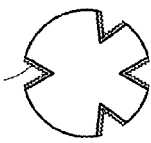
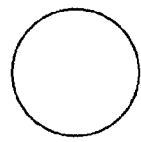
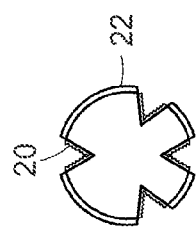
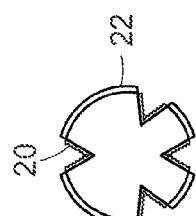

METHOD AND SYSTEM FOR MANUFACTURE AND USE OF MACROPOROUS BEADS IN A MULTIPLEX ASSAY

PRIORITY CLAIM

The present application claims priority to U.S. Provisional Application No. 61/113,027 filed Nov. 10, 2008.

BACKGROUND OF THE INVENTION

1. Field of the Invention

The present invention relates to macroporous particles especially useful in multiplex assays and to manufacturing methods and methods of use of such particles.

2. Background of the Invention

Research and development of macroporous poly (styrene-divinylbenzene) microspheres has been ongoing since the late 1950's. These macroporous microspheres have the ability to interact with atoms, ions, and molecules. Generally speaking, macroporous microspheres are microspheres with pore diameter sizes exceeding about 20 nm. The fact that these macroporous microspheres are porous yields the unique ability to form interactions on the interior "pores" as well as the exterior surface of the macroporous microspheres.

Many applications of macroporous microspheres focused on use as ion-exchange resins and in liquid chromatography. Functionalization of these macroporous microspheres has led to their use as separation media. The internal makeup of the styrene/divinylbenzene co-polymer is ideal for the introduction of and reaction with compounds and molecules with known high exchange capacities. Use for macroporous microspheres has also been found in biological applications by physical adsorption of materials of interest, commonly using reverse-phase ion exchange chromatography, although other methods are possible and have been documented. Cation-exchange resins have been prepared by functionalization of macroporous microspheres with sulfonic acid, which can be useful for acid catalysis and has been well documented in the literature.

In one method for producing macroporous microspheres, synthesis is accomplished by suspension polymerization employing an inert diluent. Once polymerization is completed, the inert diluent is removed and porous structure remained within the polymer particles. In this method, the particles produced are fairly large, but polydisperse. These characteristics are not desirable for use in chromatography where flow conditions and packing efficiency are important factors.

Another method for producing uniform polymer macroporous microspheres uses seeded emulsion polymerization to produce uniform macroporous microspheres. A modification of this method uses linear polystyrene with a solvent or non-solvent type diluent and produces macroporous microspheres with some ability to control pore volume and specific surface area, depending on whether the linear polymer is combined with a solvent or non-solvent. However, relatively high levels of crosslinker are required to generate particles with high surface area.

Analysis of clinical specimens is important in science and medicine. A wide variety of assays to determine qualitative and/or quantitative characteristics of a specimen are known in the art. Detection of multiple analytes, or separately identifiable characteristics of one or more analytes, through single-step assay processes are known, but have some limitations such as the extended times typically required to enable the detection and classification of multiple analytes and the low sensitivities (low signal) achievable in assays.

A capability to perform simultaneous, multiple interrogations of a specimen in a single assay process is known as "multiplexing" and a process to implement such a capability is a "multiplexed assay." One well known prior art technique having a multiplexed assay capability is flow cytometry. Flow cytometry is an optical technique that analyzes particular particles in a fluid mixture based on the particles' optical characteristics using an instrument known as a flow cytometer. Background information on flow cytometry may be found in Shapiro, "Practical Flow Cytometry," Third Ed. (Alan R. Liss, Inc. 1995); and Melamed et al., "Flow Cytometry and Sorting," Second Ed. (Wiley-Liss 1990), which are incorporated herein by reference.

Flow cytometers hydrodynamically focus a fluid suspension of particles into a thin stream so that the particles flow down the stream in substantially single file and pass through an examination zone. A focused light beam, such as a laser beam illuminates the particles as they flow through the examination zone. Optical detectors within the flow cytometer measure certain characteristics of the light as it interacts with the particles. Commonly used flow cytometers such as the assay system commercially available from Luminex Corporation of Austin, Tex. can measure forward light scatter (generally correlated with the refractive index and size of the particle being illuminated), side light scatter (generally correlated with the particle's size), and particle fluorescence at one or more wavelengths.

Another example of such a multiplex assay system is the xMAP® technology that is commercially available from Luminex Corporation of Austin, Tex. The xMAP technology uses a family of dyed particles onto which one or more assay-specific reagents may be applied (e.g., by coupling to one or more functional groups on the surface of the particles). The particle platform employs different sets of particles distinguishable by fluorescence. For example, the sets of particles may be distinguishable by wavelength of fluorescence, intensity of fluorescence, ratio of intensities of fluorescence at different wavelengths, etc. In general, the variation of fluorescence may be integrated by incorporating different dyes and/or fluorophores into the particles and/or coupled to a surface of the particles. In some embodiments, the sets of particles may be additionally distinguishable by size and/or shape. In any case, a particle platform having distinguishable carrier particles is generally advantageous because it uses fluid based kinetics to bind several different analytes to the assay-specific reagents.

In general, each of the different sets of particles may have a different reagent coupled thereto. The different reagents may selectively react with different analytes in a fluid sample. In other words, each of the different reagents may react with one analyte in a sample, but may not substantially react with any other analytes in the sample. In some cases, one or more additional detectable reagents may be allowed to react with one or more of the analytes. The one or more additional reagents may be detectable (and possibly distinguishable) by fluorescence (e.g., wavelength of fluorescence, intensity of fluorescence, etc.). In addition to the enhanced reaction kinetics, the use of a multiplexed assay platform advantageously allows a user to simply add or remove one or more subsets of particles, to or from the population to which the sample is exposed, to vary the analytes being investigated.

The above mentioned techniques and methods fail to take advantage of a macroporous microsphere in a quantitative single or multiplexed biological assay system.

Tuncel et al., "Electron microscopic observation of uniform macroporous particles. I. Effect of seed latex type and diluent," Journal of Applied Polymer Science, Vol. 71, No. 14, 1999, pp. 2271-2290; U.S. Pat. No. 4,459,378 to Ugelstad; and El-Aasser et al., "Synthesis and Characterization of Monodisperse Porous Polymer Particles," Journal of Polymer Science: Part A, Vol 30, 1992, pp. 235-244, describe methods of synthesizing macroporous microspheres. U.S. Pat. Nos. 7,141,431; 5,981,180; 6,632,526; 6,733,812; 7,241,883; and 7,274,316 describe various systems and methods for multiplexed biological assays. U.S. Pat. No. 6,773,812 describes methods of manufacture ad use of magnetically-responsive beads. All references cited herein are incorporated by reference as if fully set out herein to the fullest extent permissible by law or regulation.

SUMMARY OF THE INVENTION

The present invention enables the use of macroporous particles in multiplex assays and provides methods of manufacture and use. Such macroporous microspheres may be prepared by methods such as seeded emulsions, dispersion polymerizations, mini-emulsions, suspension polymerizations as well as other common techniques well known to those skilled in the art. Broadly speaking the macroporous particles hereof have a plurality of macropores where the particles are distinguishable from each other, such as by inclusion of one or more flurochromes or by virtue of size differences or light scattering properties. In a broad form, a method of performing a multiplex assay, comprises providing a group of beads in which at least some are macroporous, wherein the beads are distinguishable into at least two categories. The method of the multiplex assay includes exposing the beads to two or more analytes of interest and determining which category of bead is affected by said analyte of interest.

In general, the method of manufacturing a macroporous bead in accordance with the present invention starts with providing seed particles and mixing the seed particles with monomers and crosslinkers to swell the seed particles. The swelled particles are polymerized, such as by heating, sonication, generation of free-radicals, or other common methods well known to initiate polymerization. These are then washed with a suitable solvent to expose macropores. Preferably, only a low level of crosslinker is used (e.g., <15%) which permits easier incorporation of dyes or other distinguishing materials, such as magnetic materials.

The macroporous beads of the invention may be made uniquely distinguishable for use in multiplex assays. A distinguishable fluorochrome may be incorporated during the formation of the particle. Alternatively, fluorochromes may be associated with the particle after formation of the particle. Incorporation of materials such as dye molecules, nano-particles, liquid crystals, quantum dots, RF-transmitters, radioactive materials, magnetically responsive materials, or other similar materials can yield a particle capable of being used in a multiplex format. It is also anticipated that these microspheres can be labeled by etching an identifying code into the microsphere. These and other methods of forming distinguishable particles can be used with this invention. Fluorescence will be used as an example distinguishing characteristic in the description of the invention, but it should be apparent to those skilled in the art that any characteristic that distinguishes one particle from another is compatible with the present invention, such as the use of magnetically-responsive particles. Advantageously, the dyed macroporous beads have substantially enhanced surface area which increases the signal during a multiplex assay. In a particularly preferred form, one or more functional groups can be incorporated into the dyed macroporous beads. Advantageously, different moieties can exist between the macropores and the exterior surface area of a macroporous bead. That is, the macropores and exterior can differ by the presence or absence of a functional group, or the presence of different functional groups.

BRIEF DESCRIPTION OF THE DRAWINGS

FIG. 3 is a flow diagram illustrating the preferred method for the manufacture of a macroporous particle with functional groups added; and FIG. 4 is a flow diagram illustrating an alternative method for the manufacture of a macroporous particle with functional groups where a blocking agent is used.

DESCRIPTION OF PREFERRED EMBODIMENTS

Figure 1:
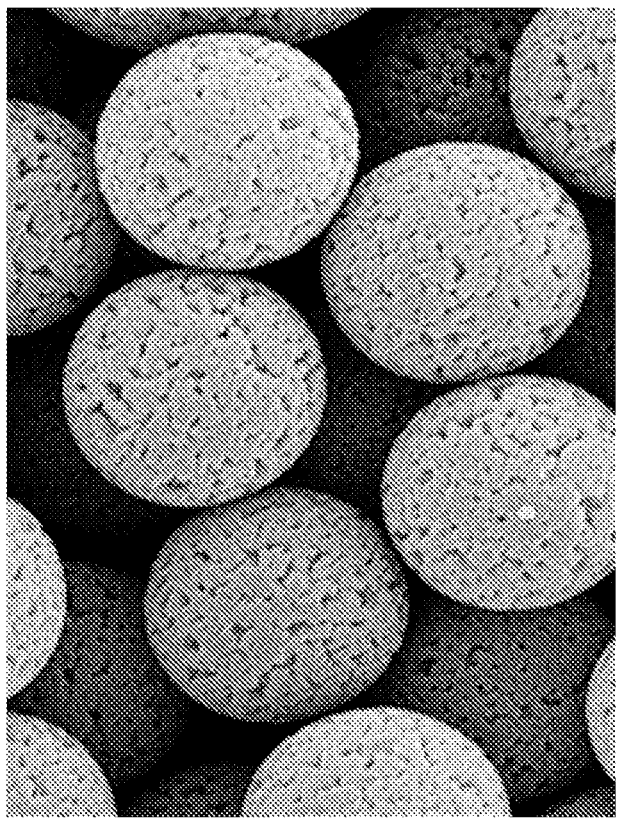
FIG. 1 is an image of macroporous particles in accordance with the present invention taken with a Scanning Electron Microscope.

Although embodiments are described herein with respect to "microspheres" or "particles" it is to be understood that the systems and methods described herein may also be used with particles, polystyrene beads, microparticles, nano-dots, nano-particles, nano-shells, beads, microbeads, latex particles, latex beads, fluorescent beads, fluorescent particles, colored particles, colored beads, organic matter, non-organic matter, or any other discrete substances known in the art. The microspheres may serve as vehicles for molecular reactions. Examples of appropriate particles are illustrated and described in U.S. Pat. Nos. 5,736,330; 5,981,180; 6,057,107; 6,268,222; 6,449,562; 6,514,295; 6,524,793; and 6,528,165 which are incorporated by reference as if fully set forth herein. The systems and methods described herein may be used with any of the microspheres or particles described in these patents. The terms "particles" and "microspheres" and "beads" are used interchangeably herein.

In addition, the types of particles that are compatible with the systems and methods described herein include particles with fluorescent materials attached to, or associated with the particles. The types of particles that can be used in the methods and systems described herein include particles having one or more fluorochromes or fluorescent dyes incorporated into the core of the particles. Also included are particle shaving fluorescent dyes or fluorescent particles coupled directly to the surface of the particles in order to provide the classification fluorescence (i.e., fluorescence emission measured and used for determining an identity of a particle or the subset to which a particle belongs). Methods used for associating fluorochromes with such particles are illustrated and described in U.S. Pat. Nos. 6,268,222 and 6,649,414 which are incorporated by reference as if fully set forth herein.

Particles that can be used in the methods and systems described herein further include particles that in of themselves will exhibit one or more fluorescent signals upon exposure to one or more appropriate light sources. Furthermore, particles may be manufactured such that upon excitation, the particles exhibit one or more fluorescent signals, each of which may be used separately or in combination to determine an identity of the particles. As described below, image data processing may include classification of the particles, particularly for a multi-analyte fluid, as well as a determination of the amount of analyte bound to the particles.

The methods described herein generally include analyzing one or more images of particles and processing data measured from the images to determine one or more characteristics of the particles, such as but not limited to numerical values representing the magnitude of fluorescence emission of the particles at multiple detection wavelengths. Subsequent processing of the one or more characteristics of the particles can be performed according to the methods described in U.S. Pat. Nos. 5,736,330; 5,981,180; 6,449,562; 6,524,793; 6,592,822; and 6,939,720 which are incorporated by reference as if fully set forth herein. In one example, techniques described in U.S. Pat. No. 5,981,180 may be used with the fluorescent measurements described herein in a multiplexing scheme in which the particles are classified into subsets for analysis of multiple analytes in a single sample.

An essential quality of a microsphere for use in multiplex assays is its ability to be uniquely distinguishable. One particularly effective method to accomplish this is to swell the porous bead comprising a polymer with an appropriate solvent doped with dye molecules or particles that can act as an identifier. In order to be successfully utilized in a quantitative multiplexed bioassay wherein the beads themselves are identified by their fluorescent signal, the beads must be swollen by a solvent suitable for the particular polymer used, as well as the dye molecule itself. This can be achieved by lightly crosslinking the bead (for e.g., by using a solution containing <about 25% crosslinker, and preferably <about 15% crosslinker) with a monomer, such as divinylbenzene, ethyleneglycoldi-methacrylate, etc. In contrast, current methods used to produce macroporous beads utilize high levels of crosslinker (e.g., >25%) in order to provide high surface area and the rigidity necessary for chromatography. Although some swelling can still take place under these conditions, it is far less than would be required to produce a bead containing adequate levels of fluorescent dye molecules to create a viable macroporous bead suitable for use in a multiplex assay.

The present invention in one aspect increases the signal and detection in a multiplex assay system by effectively increasing the surface area of the bead. A macroporous particle in accordance with the present invention is preferably synthesized utilizing a modified seeded emulsion technique. This involves synthesis of a seed particle of soluble polymer. The preferred method utilizes a seed particle prepared by any suitable method including but not limited to dispersion polymerization, emulsion polymerization, and suspension polymerization. Swelling agents are incorporated into the seed particle in order to facilitate swelling. Once the seed particles are produced they are then dispersed into a suitable solution which may contain surfactants and or stabilizers capable of emulsification of a suitable monomer.

In one method of the present invention, a single step seeded emulsion polymerization uses a linear polystyrene seed particle as the inert diluent in the production of macroporous beads. The method utilizes a low level of crosslinker; less than 15 percent divinylbenzene or any other suitable crosslinker. By including one or more fluorochromes at specific ratios in the emulsion polymerization step, particles that are individually coded by virtue of the fluorescent markers contained therein are generated.

Turning to the drawings, FIGS. 3(a)-(e) illustrates one approach for the manufacture of a macroporous particle with functional groups attached thereto to facilitate coupling of analytical species to the particle. Such particles are especially useful for performing multiplex assays, in accordance with the present invention.

(a) Mix seed particle 6 with a monomers (e.g., styrene, divinyl benzene) having functional group carrier mixed therein, as at 8, (e.g., acrylic acid, methacrylic acid to provide carboxyl groups) along with water, surfactants, and radical initiator.

Optionally incorporate a fluorochrome, magnetically responsive material, or other particulate material.

(b) Allow seed particle to swell.

(c) Apply heat to initiate polymerization.

(d) Expose the polymerized particle 10 to a carrier of the same OR different functional group 12 to form on outside of the particle 10.

(e) Wash the particle in solvent—the solvent washes out the seed polymers which are not crosslinked to form the pores 14.

In order to make the macroporous particle of the invention, the linear polymer that comprises the seed particle 6 must be of sufficient molecular weight, as is well known in the art, to be suitable to produce a final particle 10 with a macroporous structure. This parameter is generally kinetically controlled via manipulation of the rate of polymerization of the monomer 8 or by the use of chain-transfer agents. The polymerization rate can be altered by the use of different methods of radical generation or by the nature of the free-radical initiator itself, or by manipulation of the heating profile of the reaction.

Figure 2:
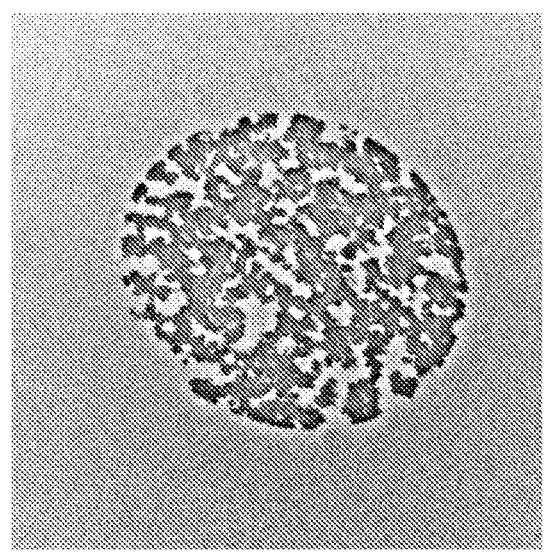
FIG. 2 is an image of a macroporous particle in accordance with the present invention taken with a Transmission Electron Microscope.

The macroporous particles 10 shown in FIGS. 1, 2, and 3 are synthesized from a variety of monomers and co-monomers. Typically, styrene, divinylbenzene, and other co-monomers such as acrylic acid, methacrylic acid, and a wide variety of other monomers are employed. A more comprehensive, but not exhaustive list of these can be found in U.S. Pat. No. 7,141,431. Preferably, the migration of monomer units into the linear polymer is dispersed in a suitable solvent capable of stabilizing the monomer and linear polymer. The monomer traverses the solvent and swells the linear polymer as much as 20-30 times and as much as 150 times or more its volume. An energy source is applied, most usually heat—(the preferred method)—which generates a free-radical cascade and generates new polymer. Other polymerization initiation methods known to those skilled in the art can be used. In the preferred particle manufacture method the monomer also contains adequate crosslinker, which once polymerized creates a crosslinked new polymer network. This new polymer is not substantially compatible with the linear polymer, which is later expelled. It is at this point that the formation of a crosslinked macroporous particle is realized.

Macroporous particles 10 can be obtained by utilization of poragens. These poragens primarily consist of solvents and non-solvents which can be introduced to swellable polymer particles. During the polymerization step, newly formed crosslinked polymer phase-separates from the poragen due to incompatibility between them. After polymerization has completed, the poragen is removed by introduction of a solvent capable of dissolving the poragen and the porous structure is obtained. In addition to the use of solvents and non-solvents as viable poragens, linear or nonlinear polymers can be used to achieve the same effect under proper conditions. More specifically, the seed particle itself can be used as the poragen when it is of a suitable molecular weight, as discussed above.

In an additional aspect of the current invention, magnetic and/or non-magnetic materials may be associated with the particles to facilitate particle handling. Some examples of these are iron oxides and complexes of iron, cobalt, manganese, gold nano-particles and others. Of the magnetic variety, they may be ferromagnetic, paramagnetic, or superparamagnetic. Alternatively, many other species well known to those skilled in the art could be used.

These materials can be associated with the particle in a variety of ways. In one method, the material can be suspended in the monomer mixture itself. Upon polymerization, the material becomes integrated into the particle. In another method, the individual salts can be introduced into the completed particle, and the desired complex can then be formed in-situ. Yet another possibility is to coat a completed particle with the desired complex. Another method of incorporating such materials is by swelling the completed particle in an appropriate solvent, such as tetrahydrofuran, chloroform, methylene chloride, benzene, or toluene. The material (e.g., magnetic material) is first coated with an organic material, such as an oleic acid, which facilitates migration. One of the reasons this is possible is because of the low levels of crosslinker (typically <about 25% and preferably <15%) used in a preferred embodiment hereof. This low level of crosslinker allows the beads to swell to a significant degree, allowing the introduction of the material. Once the magnetic and/or non-magnetic materials have been associated with the particle, the material may be overcoated with additional polymer.

The surface chemistry distributed throughout the surface of the macroporous beads of the invention creates an ideal substrate upon which to perform coupling chemistries. Coupling can be achieved through adsorption to the bead surface or covalent coupling to reactive groups on the bead surface. Methods are described for producing macroporous beads exhibiting different functional groups on the outer surface and the interior pore surfaces. It is sometimes advantageous to alter the swelling monomer to contain a moiety which may be of specific interest. Some examples of these are carboxylate, amine, imine, sulfate, and others. The specific functional group containing specie, typically a monomer, is added during the swelling of the linear polymer. One particular advantage of the macroporous particle of the present invention is the provision of a particle which contains different functionalities within the pore structure than on the outer surface of the particle. Table 1 lists common functional groups that may be used but one skilled in the art understands that Table 1 is not exhaustive and only exemplary.

| Common Functional Groups in Organic Compounds | | |
|---|---|---|
| Functional Group | Type of Compound | Suffix or prefix |
| R—$CH_3$<br>$R_1$=$R_2$<br>$R_3$≡$R_2$ | Alkane<br>Alkene<br>Alkyne | -ane<br>-ene<br>-yne |
| R—OH | Alcohol | -ol |
| $R_1$—O—$R_2$ | Ether | ether |
| R—X<br>R—$NH_2$ | Haloalkane<br>Amine | halo-<br>amine |
| R—C(=O)H | Aldehyde | -al |
| $R_1$—C(=O)—$R_2$ | Ketone | -one |
| R—C(=O)—O—H | Carboxylic acid | -oic acid |
| R—C(=O)—O—R | Ester | -oate |
| $R_1$—C(=O)—NH—$R_2$ | Amide | amide |

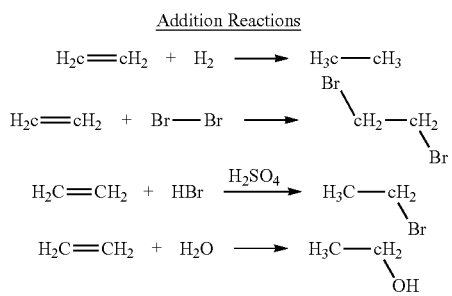

Addition Reactions $H_2C=CH_2 + H_2 \longrightarrow H_3C-CH_3$ $H_2C=CH_2 + Br-Br \longrightarrow BrCH_2-CH_2Br$ $H_2C=CH_2 + HBr \xrightarrow{H_2SO_4} H_3C-CH_2Br$ $H_2C=CH_2 + H_2O \longrightarrow H_3C-CH_2OH$ In order to produce a macroporous particle that is uniquely distinguishable, particles must be uniquely labeled. This can be accomplished in a variety of ways. In one method, particles can be modified to generate unique fluorescent signals after synthesis of the macroporous particles is complete. Alternatively, fluorochromes may be incorporated during the formation of the particles. Incorporation of materials such as dye molecules, nano-particles, liquid crystals, quantum dots, RF-transmitters, radioactive materials, magnetically responsive materials, or other similar materials can be used to yield populations of particles capable of being used in a multiplex format. Alternatively, particles can be labeled by etching an identifying code into each particle. Such uniquely identifiable particles are extremely useful in many fields, especially biological and medical type applications. As mentioned in U.S. Pat. No. 7,141,431, these particles can be analyzed manually or by other methods known, preferably using an automated technique such as flow cytometry. Alternatively, particles can be interrogated by other techniques such as absorbance, transmittance, image capture by a CMOS or CCD sensor, or other well known methods.

In prior art methods of manufacturing macroporous particles, the amount of crosslinking agent used was required to be sufficiently high to obtain a high surface area and appropriate rigidity of the particle. Levels above 40 percent and as high as 80 percent have been reported in the literature. The current invention relies on crosslinking agent at low levels, typically <25%, and preferably <15%. One advantage of using low levels of crosslinker is that it allows for the incorporation of materials such as, but not limited to dye molecules, nano-particles, liquid crystals, quantum dots, magnetic materials, or other similar materials. In such low levels of crosslinker, macroporous particles can be sufficiently swelled in a suitable solvent to allow for adequate incorporation of said materials into the particles to render them useful in multiplexed assays. Highly crosslinked particles would not be preferred for use in multiplexed assays due to their extremely limited swellability.

A particularly important aspect of the present invention is the use of populations of macroporous particles 10 in a multiplex assay, such as in flow cytometry. In a preferred embodiment, fluorescent dye molecules, which are soluble in a solvent capable of swelling a crosslinked particle, are incorporated. This can be achieved by a variety of methods, but preferably by methods described in U.S. Pat. No. 7,141,431. In the preferred embodiment, each population of particles 10 of FIG. 1 contains one or more fluorochromes at a unique concentration/ratio, resulting in distinguishable and detectable fluorescence from each population. While flow cytometry is the preferred embodiment for the multiplex assay, a variety of instrumentation could alternatively be used. Indeed, any method of determining the concentration or presence/absence of a multiplicity of analytes in a sample of a single origin using an instrument which classifies individual particles and measures the results of a reaction between an analyte and a reagent can be used.

As an alternative example, it is possible to distinguish between particles in a multiplex assay by using them in conjunction with other particles and differentiating by means of analysis of light scatter profiles. This is possible due to the fact that when combined with or "multiplexed" with a nonporous particle the light absorption and emission would be clearly different between the two. This enables the user to easily identify a particle based on the emission and scatter of the light absorbed. In addition, particles can be multiplexed together and distinguished by size of the particle. Again, light scatter profiles would be clearly distinguishable based on the size of the particle itself. Any combination of the methods mentioned above are viable alternatives. More specific examples of methods of multiplexing of particles together can be found in U.S. Pat. No. 7,141,431.

Functionalization of the Macroporous Particles

A preferred method in accordance with the present invention contemplates functionalization of the macroporous particles by incorporation of suitable co-monomers at the time of polymerization as shown in FIG. 3 and described above. It is contemplated that the surface of the particle 10 could be manipulated in such a way as to obtain two or more specific reactive moieties on a single particle. One particular approach would be to incorporate a single moiety during the polymerization step such as a vinyl co-monomer as a primary active group. Prior to removal of the poragen, seed particle, or pore-generating material, modification of the primary active group could be performed by coupling a secondary active group to the surface of the bead. Methods to perform such conjugations are well known to those skilled in the art. Once modification of the surface active groups contained on the particle surface is complete, removal of the pore-generating material results in the appearance of pores 14 containing the primary active group would still be present, and would be unmodified by the secondary active group, resulting in a particle 10 with different functionalities on the surface of the particle versus within the pores of the particle.

In another approach, instead of a second molecular species being coupled as mentioned above and illustrated in FIG. 3, a "blocking" agent could be used as generally illustrated in FIG. 4. After removal of the pore generating material the exterior of the particle would be occupied by the blocking agent while the interior pore structure would contain the primary active group. Any number of desired conjugations could be performed after which the blocked species could be further modified, creating a particle with dual functionalities.

Alternative Method for Forming Macroporous Beads w/Functional Groups (FIG. 4)

(a) Mix seed particle 6 with a monomer mixture 8 as in the method of FIG. 3
(b) Apply heat to initiate polymerization
(c) Attach "blocking agent" 16 to bead 10
(d) Wash the bead 10 in solvent 18 to form the pores 14
(e) Expose porous beads to a functional group carrier to attach functional group 20 in pore surfaces
(f) Remove blocking agent 16
(g) Optionally expose bead to a different functional group carrier to attach functional group 22 to exterior surfaces of the bead 10.

As outlined above there are many alternatives in the method of manufacture and the steps of manufacture can be performed in any order unless otherwise indicated. For example, incorporating dyes and/or magnetic materials into the bead—they can be added to the seed particle mixture or formed on the bead after the porous structure is formed.

EXAMPLES

Preparation of Seed Particle

Seed particles can be prepared in a number of ways well known to those skilled in the art. A preferred approach can be found in U.S. Pat. No. 4,459,378.

Preparation of Macroporous Particles 0.5 g of a 2 µm seed particle, 120.0 g water, 65.0 g of 1% Aerosol-OT are charged to a 500 ml flask equipped with an overhead stirrer at 125 rpm. 20.0 g distilled styrene, 1.0 g divinylbenzene, 4.5 g distilled acrylic acid, and 1.0 g of benzoyl peroxide are combined and charged to the 500 ml flask. The reaction mixture is stirred at 25° C. for 24 hours. The temperature is increased to 70° C. for an additional 24 hours. The reaction mixture is then washed with water, alcohol, and tetrahydrofuran. The completed 6 µm particles are dried under vacuum for eight hours.

Preparation of Macroporous Particles with Dual Functionality 0.5 g of seed particle, 120.0 g water, 65.0 g of 1% Aerosol-OT are charged to a 500 ml flask equipped with an overhead stirrer at 125 rpm. 20.0 g distilled styrene, 1.0 g divinylbenzene, 4.5 g distilled methacrylic acid, and 1.0 g of benzoyl peroxide are combined and charged to the 500 ml flask. The reaction mixture is stirred at 25° C. for 24 hours. The temperature is increased to 70° C. for an additional 24 hours. The reaction mixture is then washed with water and alcohol. 5 e$^6$ particles are removed and resuspended in 0.1M MES at pH 4.5. 2 µL of a 0.1 nmol/µL solution of ethylamine and 2 µL of 10 mg/mL EDC are added to the particles in MES. After 30 minutes the beads are washed with 0.02% Tween-20 and SDS and re-suspended in water. The beads are further washed in methanol and tetrahydrofuran, followed by additional washes in methanol, and re-suspension in water.

The invention claimed is:
1. A plurality of macroporous particles having pores greater than about 20 nm, wherein the exterior surface of the particles have a conjugate of a first functional group and a first analytical species and the interior of said pores have a conjugate of a second functional group and a second analytical species, wherein the interior of said pores lack said conjugate of the first functional group and the first analytical species.

2. The plurality of macroporous particles according to claim 1, wherein the plurality of macroporous particles comprises more than one population of macroporous particles and each of said populations has a distinguishable fluorescent emission.

3. The plurality of macroporous particles of claim 1, wherein the first and second functional groups are selected from the group consisting of alkane, alkene, alkyne, alcohol, ether, haloalkane, amine, aldehyde, ketone, carboxylic acid, ester, and amide.

4. The plurality of macroporous particles of claim 1, wherein the particles comprise a crosslinker.

5. The plurality of macroporous particles of claim 4, wherein the particles contain less than 25% crosslinker.

6. The plurality of macroporous particles of claim 4, wherein the particles contain less than 15% crosslinker.

7. The plurality of macroporous particles of claim 1, wherein the particles comprise polystyrene and divinylbenzene.

8. The plurality of macroporous particles of claim 1, wherein the particles further comprise a magnetically responsive material.

* * * * *